United States Patent [19]

Baldone

[11] Patent Number: 4,902,720

[45] Date of Patent: Feb. 20, 1990

[54] TREATMENT OF VIRUS INFECTIONS WITH QUATERNARY AMMONIUM COMPOUNDS

[76] Inventor: Joseph A. Baldone, 1211 Royal St., New Orleans, La. 70116

[21] Appl. No.: 214,880

[22] Filed: Jul. 5, 1988

Related U.S. Application Data

[63] Continuation of Ser. No. 19,117, Feb. 26, 1987, abandoned, which is a continuation of Ser. No. 756,666, Jul. 19, 1985, abandoned, which is a continuation-in-part of Ser. No. 743,889, Jun. 12, 1985, abandoned, which is a continuation of Ser. No. 631,645, Jul. 16, 1984, abandoned, which is a continuation-in-part of Ser. No. 456,732, Jan. 10, 1983, abandoned.

[51] Int. Cl.$^4$ .............................................. A61K 31/14
[52] U.S. Cl. ..................................... 514/642; 514/643
[58] Field of Search ................................ 514/642, 643

Primary Examiner—Stanley J. Friedman
Attorney, Agent, or Firm—Finnegan, Henderson, Farabow, Garrett & Dunner

[57] ABSTRACT

A method for preventing or treating infection or disease in a mammal caused by a virus, such as herpes simplex virus type 1 and 2. A quaternary ammonium compound, such as tetraethylammonium ion or hexamethonium ion, is administered to the mammal in an effective dosage.

13 Claims, No Drawings

TREATMENT OF VIRUS INFECTIONS WITH QUATERNARY AMMONIUM COMPOUNDS

This application is a continuation of application Ser. No. 019,117, filed Feb. 26, 1987, which is a continuation of Ser. No. 756,666, filed July 19, 1985, which is a continuation-in-part of Ser. No. 743,889, filed June 12, 1985, which is a continuation of Ser. No. 631,645, filed July 16, 1984, which is a continuation-in-part of Ser. No. 456,732, filed Jan. 10, 1983, all now abandoned.

BACKGROUND OF THE INVENTION

The present invention relates to a method for preventing or treating infection and disease in a mammal caused by a virus. More specifically, the invention relates to the administration of a quaternary ammonium compound to a mammal either before or after the virus has infected the host.

Viruses are associated with a large number of infections and diseases in mammals, such as man. Although modern medical science has developed some treatment techniques that are effective to prevent a particular disease, i.e., the polio vaccine, the art generally lacks a method by which a large number of different virus infections can be effectively prevented or treated.

Past treatments of various diseases caused by viruses have been largely ineffective. To inhibit viral replication, the growth of a virus, an agent must selectively inhibit one or more of the following specific functions: (1) adsorption, (2) uncoating, (3) transcription, (4) protein synthesis, (5) nucleic acid replication, (6) maturation, and (7) release.

For example, various agents developed in an attempt to treat Herpes Simplex Virus type 1 (HSV-1) and type 2 (HSV-2), (e.g. idoxuridine, cytosine arabinoside, adenine arabinoside, triflurothymidine, and acyclovir) all interfere with viral and host cellular functions. Because of host cell toxicity, these agents have been of very limited effectiveness for use, especially systemic, in humans to treat or prevent HSV-1 and HSV-2.

Accordingly, there is a strong need for a method that can effectively treat or prevent in a mammal infections and diseases caused by viruses, of which the above-mentioned HSV-1 and HSV-2 are merely examples. Although quaternary ammonium compounds have been known in the art, the art has failed to recognize that quaternary ammonium compounds can effectively treat and prevent in mammals infections and diseases associated with a variety of viruses, including HSV-1 and HSV-2. Quaternary ammonium compounds are analogous to ammonium salts in which organic radicals are substituted for all four hydrogens of the original ammonium cation.

Although tetraethylammonium chloride (TEAC), a quaternary ammonium compound, was briefly advocated for use in the 1950s to treat the pain associated with herpes zoster, this recommendation was subsequently abandoned. Thus, there was no recognition in the art that TEAC could be used to treat infections and diseases caused by a variety of other viruses.

Notwithstanding the long period during which quaternary ammonium compounds have been known and studied, the art has failed to recognize the ability of quaternary ammonium compounds to treat or prevent infections and diseases in a mammal caused by a virus. Similarly, the art has lacked any realization that quaternary ammonium compounds can produce an antiviral effect or inhibit the viral function in a mammal.

SUMMARY OF THE INVENTION

Quite surprisingly, the present inventor has discovered a method that effectively treats or prevents infections and diseases in mammals caused by a number of viruses. More particularly, the present invention provides a method for preventing or treating infection and disease in a mammal caused by a virus comprising the step of administering to the mammal a quaternary ammonium compound in an effective dosage. However, when the virus is herpes zoster, the quaternary ammonium compound is not tetraethylammonium chloride (TEAC).

The present invention also provides a method of treating a mammal comprising the step of administering to the mammal a quaternary ammonium compound in a dosage effective to produce an anti-viral effect with respect to a virus. In this method, when the virus is herpes zoster, the quaternary ammonium compound is not TEAC.

In another embodiment, the present invention provides a method of treating a mammal comprising the step of administering to the mammal a quaternary ammonium compound in a dosage effective to inhibit the viral function of a virus. Similarly, when the virus is herpes zoster, the quaternary ammonium compound is not TEAC.

In the present invention, the quaternary ammonium compound is preferably selected from tetraethylammonium ion, hexamethonium ion, pentolinium ion, chlorisondamine ion, trimethidinium ion, trimethaphan ion, and homologs thereof. Preferably, the virus is an adenovirus, an arbovirus, an arena virus, a bacteriophage, a coliphage, a coronavirus, a hepatitis virus, a herpetovirus, an oncogenic virus, an orthomyxovirus, a papovavirus, a paramyxovirus, a parvovirus, a picornavirus, a plant virus, a pox virus, a reovirus, a retrovirus, a rhabdovirus, and a togavirus.

The present invention overcomes some of the disadvantages commonly associated with previous methods of treating or preventing virus infections and diseases and obtains the various advantages of the invention. By administering a quaternary ammonium compound to a mammal infected by a virus, the present method treats or prevents infections and diseases caused by the virus. Moreover, the quaternary ammonium compound, when administered to the infected mammal, produces an antiviral effect or inhibits the viral function of the virus.

These and other features and advantages of the present invention will be made more apparent from the following description of the preferred embodiments.

DETAILED DESCRIPTION OF THE PREFERRED EMBODIMENTS

The present invention provides a method for preventing or treating infection or disease in a mammal caused by a virus. In the method, a quaternary ammonium compound is administered to a mammal in an effective dosage. However, when the virus is herpes zoster, the quaternary ammonium compound is not TEAC.

The quaternary ammonium compounds for use in the present invention can be any compound that has a central nitrogen joined to four organic groups capable of treating or preventing infection in a mammal caused by a virus. The organic groups on the central nitrogen can be alkyls, aryls, aralkyls, aliphatics, alicyclics, heterocyclics, aromatic cyclics, alcohols, ethers, esters, aldehydes, ketones, sulfonamides, carboxylic acids, and carbohydrates. The central nitrogen may also form a ring with one or more of the organic groups. The organic groups may be the same or different depending upon the particular compound.

The quaternary ammonium compound can be a simple monoquaternary ammonium compound, such as tetraethylammonium chloride (TEAC); a complex monoquaternary ammonium compound, such as phenacyl homatropinium; a bis-quaternary ammonium compound, such as pentamethonium chloride, hexamenthonium chloride, and pentolinium tartrate; and an asymmetrical diquaternary ammonium compound such as trimethidinium methasulfate and chlorisondamine chloride.

The aliphatic groups on the central nitrogen can be alkanes, olefins, or alkynes. The cyclic groups can be alicyclics, aromatics, and heterocyclics.

For example, the organic groups on the central nitrogen can be alkyls having 1 to 20 carbon atoms, hydroxalkyls, aminoalkyls, alkenyls, or substituted derivatives thereof, especially methyl, ethyl, propyl, isopropyl, butyl, isobutyl, allyl, and methylallyl groups. The alicycles and heterocyclic groups can be cyclohexyl or cyclopentyl groups, which may be attached directly or through a side chain to the nitrogen atom. The organic groups on the central nitrogen can also be hydrophobic aliphatics, unsaturated aliphatics, or aliphaticaryl radicals. The hydrophobic aliphatics may be long-chain alkyl, long-chain alkoxyaryl, long-chain alkylaryl, halogen substituted long-chain alkylaryl, long-chain alkylphenoxyalkyl, and arylalkyl.

The organic groups also can be a low molecular weight group such as furfuryl, tetrahydrofurfuryl, alkyl, carbethoxyalkyl, hydroxalkyl, aminoalkyl or alkenyl groups. The organic groups can also be a high molecular weight aliphatic hydrocarbon group, which may be saturated or unsaturated and may be a forked or a straight chain. Samples of these groups include myristyl, cetyl, stearyl, and oleyl. These groups may also contain substituents, such as hydroxyl, halogen, carbethoxy and amino.

The organic groups can also be joined together so as to form a heterocyclic ring when both ends of an organic group are attached to the central nitrogen atom. Examples of such rings include pyridine, piperidine, picoline, pipecoline, pyrrol, pyrrolidine, morpholine, quinoline, quinaldine, azole, thiazole, and substituted derivatives thereof.

Examples of the various quaternary ammonium compounds useful in the invention include alkyl ammonium halides, such as cetyl trimethyl ammonium bromide and dioctadecyl dimethyl ammonium chloride; alkyl aryl ammonium halides, such as octadecyl dimethyl benzyl ammonium chloride; N-alkyl-pyridinium halides, such as N-laurylpyridinium chloride; quaternary ammonium salts containing ether linkages in the molecule, such as paratertiary octylphenoxyethoxyethyl dimethyl benzyl ammonium chloride; quaternary ammonium compounds having oxygen in the form of amide or ester linkages, such as N-(laurylcolaminoformylmethyl) pyridinum chloride; quaternary ammonium compounds containing a sulfonamide group, such as 2-phenyl-3-p-sulfamido-phenyl-5-undecyltetrazolium chloride; and quaternary ammonium compounds having a substituted aromatic nucleus, such as lauryloxyphenyl trimethyl ammonium chloride, dodecylbenzyl trimethyl ammonium chloride, chlorinated dodecylbenzyl trimethyl ammonium chloride, dodecylphenyl trimethyl ammonium methosulfate, and the like.

The anion of the quaternary ammonium compound can be any anion that is compatible with the central nitrogen and the four organic groups of the compound. Typical anions include —Cl, —Br, —I, —NO$_3$, =SO$_4$, —CO$_2$CH$_3$, —C$_6$H$_5$SO$_3$, —OH, =PO$_4$, —CO$_2$C$_6$H$_5$, =CO$_3$, —HO—C$_6$H$_4$CO$_2$, and dicarboxylic acids and tricarboxylic acids, such as tartaric and citric acids, and fatty acids.

The preferred quaternary ammonium compounds have the following chemical formulas:

TABLE 1

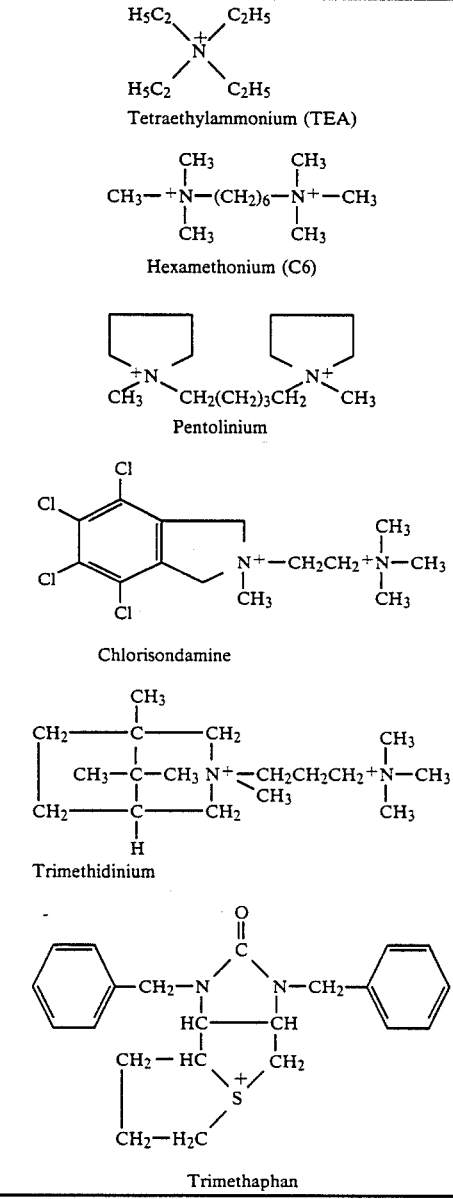

However, as noted, other quaternary ammonium compounds known in the art can also be used.

The diversity of quaternary ammonium compounds useful in the present method is illustrated in Table 1 above. The chemical configurations include simple monoquaternary ammonium compounds such as etraethylammonium chloride (TEAC); complex monoquaternary ammonium compounds such as phenacylhomatropinium; bis-quaternary ammonium compounds such as pentamethonium chloride, hexamethonium chloride, and pentolinium tartrate; asymmetrical diquaternary ammonium compounds such trimethidinium methasulfate and chlorisondamine chloride; and complex monosulfonium compounds such as trimethaphan camphorsulfonate. The quaternary ammonium compounds can be made by numerous methods known in the art. For example, U.S. Pat. No. 2,653,156 to Deutsch et al. discloses how to prepare TEAC.

The present method can be used to treat or prevent infection and disease in a mammal caused by any virus by administering to the mammal an effective dosage of a quaternary ammonium compound that is effective against that particular virus. Once taught the present invention, one skilled in the art can readily select the appropriate quaternary ammonium compound for a particular virus without undue experimentation. For example, TEAC or HMB can be effectively used to treat or prevent infections and diseases caused by HSV-1 and HSV-2. However, when the virus is herpes zoster, the selected quaternary ammonium compound is not TEAC.

Preferably, the present method is used to treat or prevent infections and diseases caused by a virus selected from the group consisting of adenoviruses, arboviruses, arena viruses, bacteriophages, bunya viruses, coliphages, coronaviruses, hepatitis viruses, herpetoviruses, oncogenic viruses, orthomyxoviruses, papovaviruses, paramyxoviruses, parvoviruses, picornaviruses, plant viruses, pox viruses, reoviruses, retroviruses, rhabdoviruses, and togaviruses. Examples of these viruses are listed in Table 2. This list, however, is not meant to be inclusive. Hence, infections and diseases in mammals caused by other viruses that can be treated or prevented by administering a quaternary ammonium compound to the mammal are within the scope of the present invention.

TABLE 2

| Virus Family | Examples of Virus |
| --- | --- |
| Adenovirus | |
| Arbovirus | |
| Arenavirus | |
| Bacteriophages | T2, T4, T6 |
| Bunyavirus | |
| Coliphages | R17, T3, T5, T7 |
| Coronavirus | |
| Hepatitis | Hepatitis A, B, C |
| Herpetovirus | Herpes Simplex 1, Herpes Simplex 2, Cytomegalovirus Epstein-Barr, Varicella |
| Oncogenicvirus | Retrovirus |
| Orthomyxovirus | Influenza A, B, C Parainfluenza |
| Papovavirus | Polyoma Papilloma SV 40 |
| Paramyxovirus | Newcastle disease Parainfluenza Subacute schlerosing panencephalitis Rubeola Mumps Sendai Morbillivirus Pneumovirus Measles Canine Distemper |
| Parvovirus | Adeno assoc. |
| Picornavirus | Oliphage Enterovirus Polio Coxsackievirus Echovirus Enterovirus Rhinovirus Hoof & Mouth Disease |
| Plant Virus | Tobacco Mosaic Turnip Yellow Rice Dwarf Beet Yellow |
| Pox Virus | Variola Vaccinia Contagious Dermatitis Cow Pox Molluscum Contagiosum Paravaccinia Tana Pox |
| Reovirus | Orbivirus Rotavirus Cytoplasmic Polyhedrosis |
| Retrovirus | Sarcoma Leukemia Lymphoma Carcinoma |
| Rhabdovirus | Rabies Marburg |
| Togavirus | Encephalitis Alphavirus Flavivirus Rubivirus Rubellavirus Yellow Fever |

Descriptions and structures of many of the viruses listed in Table 2 are provided in Davis et al., *Microbiology, Including Immunology & Molecular Genetics* (3rd ed) 853-1262 (1980) and Rose, et al., *Manual of Clinical Immunology* (2d ed.) 612-713 (1980), which are incorporated herein by reference. Cultures of many of these viruses can be obtained from the American Type Culture Collection (ATCC) in Rockville, Maryland.

When the appropriate quaternary ammonium compound is administered to a mammal, such as a human, a monkey, a mouse, or a dog, infected by one of these viruses, the treatment prevents or treats infections or diseases caused by the virus. Additionally, the administration of the quaternary ammonium compound can achieve one or more other effects, including preventing or reducing the shedding of the virus; preventing the recurrence of the disease caused by the virus in the case of viruses causing recurring diseases; reducing the frequency of the recurrence of symptoms of the disease in the case of viruses causing recurring diseases; reducing the duration of symptoms of the disease; or reducing the severity of the symptoms.

In one embodiment, the quaternary ammonium compound is administered to the mammal in a dosage effective to produce an anti-viral effect with respect to the virus. In another embodiment, the quaternary ammonium compound is administered to the mammal in a dosage effective to inhibit the viral function of the virus. Of course, the same administration of the quaternary ammonium compound to a mammal can achieve simultaneously many, if not all, of these effects.

One skilled in the art can select the appropriate quaternary ammonium compound and the appropriate dosage to produce these effects with respect to a particular infection or disease. For example, TEAC can be administered to humans infected by HSV-1 or HSV-2 to achieve these desirable effects.

The quaternary ammonium compounds can be administered to a mammal, such as man, in a number of pharmaceutically acceptable manners, such as intravenously, intramuscularly, parenterally, topically, orally and/or vaginally. The particular quaternary ammonium compound to be selected depends on many factors including the virus implicated, the host, and the proposed method of administration.

The quaternary ammonium compound will usually be present in a pharmaceutically effective carrier or diluent, such as normal sterile saline solution for systemic use or hydrophilic ointment bases for topical and vaginal administration. The concentration of the quaternary ammonium compound is limited only by the amount that may be carried or dissolved in the carrier or diluent, but preferably is in the range from about 1 to about 1000 mg per ml (total volume), more preferably in a range of from about 50 to about 250 mg/ml. In an ointment, the concentration of the quaternary ammonium compound may range from 0.01% to 99% of volume.

The dosages of the quaternary ammonium compound can be readily determined by the skilled artisan. For example, about 200 mg to about 500 mg of TEAC are intravenously administered to a human infected with HSV-1 or HSV-2, but not in an amount to exceed 7 mg per kg of body weight. The intramuscular dosage of TEAC in adult humans is 1,000 mg to 1,200 mg, but not to exceed 20 mg per kg of body weight.

The quaternary ammonium compound can also be encapsulated or placed in a pill form for oral administration to the host.

In one embodiment, the quaternary ammonium compound is preferably also a ganglionic blocker or ganglionic blocking agent, which are drugs that block transmission in autonomic ganglia without producing any preceding or concomitant change in the membrane potentials of the ganglion cells. Ganglionic blockers also do not modify the conduction of impulses in the preganglionic or postganglionic neurons and they do not prevent the release of acetylcholine (ACh) by preganglionic impulses. Ganglionic blockers produce ganglionic blockade by occupying receptor sites on the ganglion cells and stabilizing the postsynaptic membranes against the actions of ACh liberated from the presynaptic nerve endings.

Various secondary effects are also related to the ganglionic blocking function. These effects include the lowering of blood pressure to pronounced vasodilator action, mydriasis (pupil dilation), cycloplegia, which may cause temporary blurred vision, ptosis and similar impairment of physical responses that are generally associated with nerve impulse blocking action.

The preferred quaternary ammonium compounds that are ganglionic blocking agents include tetraethylammonium ion, hexamethonium ion, pentolinium ion, chlorisondamine ion, trimethidinium ion, trimethaphan ion, and homologs thereof. An appropriate anion, such as chloride or bromide, is present with the ganglionic blocking agent in the pharmaceutical preparation.

In one embodiment, the present invention provides a method for the treatment or prevention of infections or diseases caused by HSV-1 and HSV-2. In such a treatment, quaternary ammonium compounds, such as TEA ion or homologs thereof, are administered to an infected or diseased mammal to prevent or treat infections or diseases resulting from the HSV-1 and HSV-2.

Infection and disease by HSV-1 is typically associated with oral, facial and ocular lesions. Infection and disease by HSV-2 usually result in genital and anal lesions.

Both HSV types 1 and 2 show a predilection for ectodermal tissues, as evidenced by their production of lesions in the skin, oral cavity, vagina, conjunctiva and the nervous system. HSV-2, which is usually transmitted venereally, is now epidemic in the United States. Some twenty million persons are presently afflicted with this disease in this country. New cases and recurrences exceed 500,000 annually. HSV-2 infections often cause blindness, neonatal deaths, and encephalitis.

An important characteristic of HSV-1 and HSV-2 is their ability to persist in a latent or quiescent form in man and animals. Initial or primary infections by HSV-1 and HSV-2 are contracted through breaks in the mucous membrane in which the viruses replicate locally. From the membranes, the HSV-1 and HSV-2 spread to the regional lymph nodes and, occasionally, they can invade the bloodstream producing viremia. When the primary infection subsides or recedes, the virus persists in a latent form in the sensory ganglia that innervate the site of primary infection. In ocular or oral infections, the HSV-1 and HSV-2 persist in the trigeminal ganglia. In genital infections, the viruses persist in the sacral ganglia.

Although the state of the viral genome during latency is not yet known, latency can be upset resulting in viral multiplication of HSV-1 and HSV-2. This multiplication produces the second or recurrent form of the disease. Recurrences usually occur at the primary sites. In humans, such recurrent disease and infection are typically induced by heat, cold, sunlight, ultraviolet light, hormonal and emotional disturbances, or immunosuppressive agents.

Epidemiological control of HSV-1 and HSV-2 is presently poor, because the majority of the population, up to 95%, has been exposed to the viruses. In the healthy carrier, the viruses can be isolated in various fluids, such as tears, saliva, and vaginal secretions, even during the absence of overt disease.

Recurrences of HSV-1 and HSV-2 have been experimentally produced in animals by a variety of stimuli, including physical manipulation of the sensory ganglia. In all cases of reactivation, a change is seen in the reservoirs of the ganglia. The present inventor has found that quaternary ammonium compounds have a profound effect on inhibiting the recurrence of infection and diseases caused by HSV-1 and HSV-2.

The following examples demonstrate that quarternary ammonium compounds are effective in treating diseases and infections caused by viruses, especially HSV-1 and HSV-2.

EXAMPLE NO. 1

In the following experiments, the antiviral activity of two quaternary ammonium compounds, tetraethylammonium chloride (TEAC), a TEA ion, and hexamethonium bromide (HMB), were tested. The tests showed that these compounds inhibit the in vitro replication of HSV-1 and HSV-2.

The experiments in Example No. 1 were divided into three (3) series. The first and second series of experiments in Example No. 1 evaluated the antiviral activity of (TEAC), a monoquaternary ammonium compound. The antiviral properties of TEAC were determined particularly with respect to the in vitro inhibition of HSV-1 and HSV-2 replication. The third series of experiments in Example No. 1 determined the antiviral activity of hexamethonium bromide (HMB), a bis-quaternary ammonium compound.

In Series No. 1 of Example No. 1, monolayer cultures of Vero, RK-13 (rabbit kidney), and WISH (human amnion, Hayflick) cells were used in the experiments of Example No. 1. The cells were grown in Basal Minimal Eagle's Media supplemented with 5% fetal calf serum, 1% glutamine, sodium bicarbote and antibiotics. Cultures were maintained in a maintenance media that was the same media, except that the maintenance media contained 2% fetal calf serum. An F Strain of HSV-1 was chosen because it is a well-known prototype of HSV-1. This F Strain can be obtained from the American Type Culture Collection (ATCC), 12301 Parklawn Drive, Rockville, MD 20852, at which it is identified as ATC-VR 733. For studies with HSV-2, a G strain of HSV-2 (ATCC-VR 734) and a 333 strain of HSV-2 were selected. These strains also can be obtained from the ATCC.

Two methods were used to test the drug's effectiveness in the suppression of viral growth. In the pre-inoculation experiments, the drug was added after adsorption of the virus. In the pre-incubation experiments, the drug was added prior to infection of the cell cultures.

Accordingly, the pre-inoculation experiments measured the effect of the drug on a cell that was already infected with the virus. The pre-incubation experiments measured the cell cultures that were treated with the drug prior to the inoculation to determine if these cells then would be permissive or non-permissive to the tested virus. In these experiments, plaque reduction assays provided a quantitative measure of antiviral activity and was deemed to be reliable and objective.

In the pre-inoculation experiments, monolayer cultures of WISH cells were grown in either 25 cm$^2$ plastic flasks or 6 well cluster dishes and were inoculated with 0.2 ml of the virus strain. The cells were allowed to adsorb the virus for 45 minutes at 37° C., with gentle rocking of the cultures every 15 minutes.

After the adsorption period, 1 ml of the drug and 3 ml of the maintenance media were added to each well. Also after the absorption period, 1 ml of the drug and 4 ml of the maintenance media were added to the 25 cm$^2$ plastic flasks. All cultures were prepared in duplicate.

In the pre-incubation experiments, the media was either decanted or gently aspirated from the cultures. After decanting or aspirating, 1 ml of the drug dilution plus maintenance media was added to the cultures. The cultures that served as virus controls or cell controls received 2 ml of maintenance media. After the pre-treatment period, the media was again aspirated and the cell cultures were infected with the virus.

The cultures were incubated at 37° C. for 36–38 hours or until the virus control showed discrete visible plaque. When this occurred, the cultures were fixed and stained with crystal violet. The plaque were then carefully counted under the microscope. By such a counting and careful comparison, percentages of plaque inhibition in the treated cultures were then calculated.

To determine the toxicity level of the drug, all three cell lines—RK-13, Vero cells, and WISH cells—were used. In the toxicity experiments, the effect of the drug on the uninfected cell for a range of periods of time was determined. Accordingly, cultures were incubated with and without the drug. The time of exposure was from one to seven hours. A comparison was then made between the drug treated cultures and the control cultures. After each period of incubation, the cells were washed and fresh media was added to the cells. The cell viability was then determined by dividing these cultures and having them grow into new cell cultures.

The apparent toxicity that was described as thin was totally reversible. When the drug was removed and fresh media added, the cell layer reverted to its normal non-treated appearance.

No change in morphology or cytopathic effect was seen in the cultures containing TEAC nor those without TEAC. There was no difference in the rate of growth between TEAC-tested cultures and cultures without TEAC. These observations indicate that TEAC is not toxic to cells.

All drug dilutions in the experiments were made in maintenance media.

These methods and materials were used in all of the experiments of the first series of Example No. 1.

A. FIRST SERIES

Experiment 1A

The effect of TEAC on monolayer cultures of Vero and WISH cells was tested to determine the toxicity limits of the drug. Confluent monolayer cultures of 25 cm$^2$ plastic bottles were incubated overnight at concentrations of 5 mg, 2.5 mg and 1.25 mg of TEAC per culture. No change in the morphology of the cells was seen.

At the end of the incubation period, the cultures were washed twice with sterile PBS (Dulbecco). Fresh medium was added to each of the cultures. The cultures were then incubated for an additional 24 hours. There was no apparent difference in the growth or general appearance between the treated and the untreated controls.

Experiment 1B

Confluent monolayer cultures of Vero cells were infected with the F strain of HSV-1. After the adsorption of the virus by the cells, the cultures received 1 ml of TEAC at a concentration of 2.5 mg/ml plus 4 ml of maintenance media. The control cultures received no drug. The cultures were stained at the appropriate time and the plaque were counted.

Drug-treated cultures had an average of 75.5 plaque and the control cultures had an average of 488.5 plaque. Therefore, the rate of plaque inhibition was 84%. In addition, the size of the plaque was appreciably smaller in the drug treated cultures as compared to the control cultures.

Experiment 1C

Confluent monolayer cultures of WISH cells were infected with the F Strain of HSV-1, as in Experiment 1B. The dilutions of TEAC tested were 10 mg/ml, 5 mg/ml, 2.5 mg/ml and 0.65 mg/ml. After the adsorption of the virus by the cells for 45 minutes, 1 ml of TEAC dilution plus 3 ml of maintenance media was placed into each of two wells.

In another plate, duplicate wells received 1 ml of TEAC dilution plus 1 ml of maintenance media. These duplicate wells were incubated for 3 hours. After this time, the maintenance media was aspirated and the cultures were infected. Fresh maintenance media was then added. The cells were incubated at 37° C. until discrete plaque were observed in the control wells.

The findings of experiment 1C are presented in Table 3. The findings can be summarized as follows:
1. Antiviral activity was seen in all dilutions tested.
2. When the drug was added after inoculation with the virus, there was no strict correlation between the viral inhibition and dosage. For example, TEAC concentrations of 5 and 2.5 mg/ml, which differ by a factor of 2, gave similar degrees of inhibition, namely, 45% and 46%.
3. Pre-incubation of the cell monolayer with 100 mg/ml of TEAC prior to inoculation with the virus gave 71% plaque inhibition. Pre-incubation of the cell monolayer with 5 mg and 2.5 mg of TEAC prior to inoculation gave 22% and 10% plaque inhibition.

TABLE 3
EFFECT OF TEAC ON HSV REPLICATION
(HSV-1 - F STRAIN)

A. Drug added after inoculation with virus

| mg/culture | % plaque inhibition |
|---|---|
| 10.00 | 56 |
| 5.00 | 45 |
| 2.50 | 46 |
| 1.25 | 39 |
| 0.62 | 30 |

B. 3 hours pre-incubation

| mg/culture | % plaque inhibition |
|---|---|
| 10.0 | 71 |
| 5.0 | 22 |
| 2.5 | 10 |

As seen in Table 3, pre-incubation of the cells with 10 mg/ml solution of the drug rendered the cells non-permissive to the virus, as shown by the 71% plaque inhibition. When the TEAC was added after inoculation of the culture with HSV-1, significantly different drug dilutions from 10 mg/culture to 0.62 mg/culture yielded similar degrees of plaque inhibition. Consequently, without being bound by theory, it is believed that the mode of action of TEAC is other than by viral metabolic process.

Experiment 1D

Experiment 1D used the same method and materials as Experiment 1C except that the TEAC drug concentrations were increased by a factor of ten. The results are presented in Table 4.

TABLE 4
EFFECT OF TEAC ON HSV REPLICATION
(HSV-1 - F SRAIN)

| mg/culture | % plaque inhibition A | % plaque inhibition B |
|---|---|---|
| 100.0 | toxic | 79 |
| 50.0 | 100 (thin) | 82 |
| 25.0 | 100 (thin) | 79 |
| 12.5 | 62 | 80 |
| 6.2 | 20 | Not Done |

A. Drug added after virus adsorption.
B. Cultures re-incubated with the drug for 3 hours prior to infection.

Thus, the results of Experiment 1D confirmed the findings of Experiment 1C. Pre-incubation of the cells with several dilutions of the TEAC drug gave comparable degrees of plaque inhibition. Those cultures that received the drug prior to inoculation gave relatively the same degree of protection (79%-82%), regardless of the TEAC concentration.

In the other cultures in which the drug was added after the adsorption period, the following was found: 10 mg/culture was toxic and the cells lifted off the plate. At the next concentrations, 50 and 25 mg/culture, no plaque formed, but the cell layer was "thin." As used herein, the term "thin" means that the cells were still attached to the container, but the monolayer was not confluent and there were spaces between the individual cells. The 62% plaque-inhibition observed in the cultures containing 12.5 mg/culture of TEAC was consistent with the 56% plaque inhibition at 10 mg/culture of TEAC in Experiment 1C.

Experiment 1E

In this experiment, the antiviral activity of TEAC was tested at different concentrations of the drug and at different preincubation periods using the above noted methods and materials.

WISH cells were pre-incubated with 100 mg, 50 mg, 25 mg, 12.5 mg and 6.2 mg of TEAC per culture for 2, 4, and 7 hours prior to infection with HSV-1 (F strain). The results of experiment 1E are set out in Table 5.

TABLE 5
EFFECT OF TEAC ON HSV REPLICATION
(HSV-1 - F strain)

| Pre-incubation time | mg/culture | % plaque inhibition |
|---|---|---|
| 2 hours | 100.00 | 68 |
| 2 hours | 50.00 | 24 |
| 2 hours | 25.00 | 17 |
| 2 hours | 12.50 | 18 |
| 2 hours | 6.25 | 0 |
| 4 hours | 100.00 | 100 (thin) |
| 4 hours | 50.00 | 63 |
| 4 hours | 25.00 | 37.5 |
| 4 hours | 12.50 | less than 20 |
| 4 hours | 6.25 | less than 20 |
| 7 hours | 100.00 | 100 (thin) |
| 7 hours | 50.00 | 95.7 |
| 7 hours | 25.00 | 96.5 |
| 7 hours | 12.50 | 76 |
| 7 hours | 6.25 | 50 |

In these controlled experiments, antiviral activity was observed to be dependent on both concentration and duration of exposure to the TEAC. For example, the percent inhibition ranges between 17% and 96.5% at 25 mg/culture.

Experiment 1F

The effect of TEAC was tested on cultures infected by HSV-2 in accordance with the above noted method. The 333 strain, which can be obtained from ATCC, was used. Table 6 below shows the results of this experiment.

The percent inhibition of 56% with 50 mg/culture at a preincubation time of 2 hours is consistent with the results found with HSV-1. Based on the results in Table 6, HSV-2 (333 strain) appeared to be even more sensitive to TEAC than HSV-1. The G strain of HSV-2, obtainable from ATCC, was also tested and gave similar results.

TABLE 6
EFFECT OF TEAC ON HSV REPLICATION
(HSV-2-333 STRAIN)

| Pre-incubation time | mg/culture | % plaque inhibition |
|---|---|---|
| 2 hours | 50.00 | 56 |
| " | 25.00 | 42 |
| " | 12.50 | 25 |
| " | 6.25 | 0 |

In summary, Experiments 1A to 1F in the first series of Example No. 1 showed that:

(a) TEAC inhibited the in vitro replication of HSV-1 and HSV-2.

(b) The antiviral effect of TEAC was present whether it is added before or after viral inoculation.

(c) When TEAC was added before viral inoculation, it rendered the cells non-permissive to the virus and no plaque formed. In these experiments, the antiviral activity was time and dosage dependent.

(d) Suppression of viral growth was evidenced not only by the reduced number of plaque, but also by their reduced size.

(e) Without being bound by theory, the mode of action of TEAC does not appear to involve impairment of the cell metabolic process.

(f) The observed toxicity or changes in the cell's morphology was totally reversible.

B. SECOND SERIES

Experiment 1G

Confluent monolayer cultures of vero cells were infected with varying amounts of HSV-1 (McKrae strain) and allowed to adsorb for 30 minutes prior to the addition of TEAC. All cultures were incubated at 37° C. in a 5% $CO_2$ humidified atmosphere. The cultures were stained with crystal violet to aid in counting the plaque.

TABLE 7
DRUG RESPONSE CURVE

| mg/ml | No. of Plaques |
| --- | --- |
| 50.000 | Cells lifted off |
| 25.000 | 0 |
| 12.500 | 300 |
| 6.250 | 286 |
| 3.125 | 247 |
| VC | 270 |
| VC | 270 |
| VC | 252 |

As shown, the highest concentration (50 mg/ml) was toxic and the cells lifted off and died. The second concentration (25 mg/ml) was tolerated, but the monolayer had a thinned out appearance. The rest of the concentrations was not significantly effective in achieving plaque inhibition.

The data in Table 7 suggests the apparent enhancement of plaque found in the cultures that received 12.5 mg/ml of the drug. Investigations were then made of other concentrations that would give good antiviral activity but less toxicity and a working concentration of 20 mg/ml of TEAC was determined.

Experiment 1H

To determine whether TEAC physically inactivates the virus prior to entry into the cell, experiment 1H was conducted. An aliquot of a virus suspension was mixed with TEAC to yield a final concentration of 20 mg/ml. A similar aliquot without the drug, but in the same volume, was prepared as a control. Both mixtures were maintained at 4° C. for 30 minutes, 60 minutes, or 90 minutes. 0.3 ml of the solutions were plated onto susceptible cell cultures and incubated at 37° C. for 36 hours. All cultures were stained and compared to the virus control.

There was no discernible difference between the control group and the TEAC-treated group. This indicated that incubation of the cell-free virus with TEAC does not inactivate the virus. The results are summarized in Table 8.

TABLE 8
EFFECT OF TEAC ON CELL FREE VIRUS

| Time | Drug-treated | Control |
| --- | --- | --- |
| 30 min. | 265 | 273 |
| 60 min. | 260 | 272 |
| 90 min. | 258 | 274 |

Experiment 1I

Previously, cell toxicity at higher concentrations of TEAC in the range of 50 and 25 mg/ml was reported. To invesitgate the degree of toxicity in other cells, TEAC and Hexamethonium Bromide (HMB) at 25 mg/ml were tested. Healthy confluent monolayer cell cultures were overlaid with 1 ml of the drug and incubated for 48 hours at 37° C. and then stained. Cell cultures with maintenance media were used as controls. The results were as follows:

(a) RK-13 cells showed toxicity with TEAC and slight toxicity with HMB;

(b) Flow 1000 cells (foreskin cells) showed toxicity with TEAC and no toxicity with HMB; and (c) Vero cells showed slight toxicity with TEAC and no toxicity with HMB.

Consequently, it appeared that the toxicity was host cell dependent.

Experiment 1J

Large numbers of cultures were infected with HSV-1. After virus adsorption, maintenance media containing 20 mg/ml of TEAC was added. At varying times, the TEAC was removed and fresh media without TEAC was added to the cultures.

TABLE 9
ANTIVIRAL ACTIVITY OF TEAC

| TEAC removed | PFU/ml | % Reduction |
| --- | --- | --- |
| 4 hours P.I. | 1042 | 25% |
| 6 hours P.I. | 596 | 57% |
| 8 hours P.I. | 436 | 69% |
| 10 hours P.I. | 163 | 88% |
| Virus Control | 1398 | |

Therefore, a significant reduction in plaque was achieved at 10 hours P.I. as shown by 88% plaque inhibition.

Experiment 1K

This experiment attempted to measure the antiviral activity of TEAC expressed as total virus yield. In experiment 1K, cultures were infected with the McKrae strain of HSV-1 at a high multiplicity of infection. At 4 hours post infection, when viral replication was underway, TEAC at a concentration of 20 mg/ml was added to the cultures. At designated times, the cultures were harvested. The supernatant fluid and the cells were kept separate to assay for viruses released in the supernatant fluid and also that present in the cells. Both supernatant fluid and the cells were frozen immediately at −85° C. These samples were then assayed for infectious particles on susceptible cells. The results are shown in Table 10.

TABLE 10
VIRUS YIELD FROM TREATED AND NON-TREATED RE INFECTED CELLS IN PFU/m SUPERNATANT

TABLE 10-continued
VIRUS YIELD FROM TREATED AND
NON-TREATED RE INFECTED CELLS IN PFU/m

| Time P.I. | TEAC | | | Control | | |
|---|---|---|---|---|---|---|
| | $10^{-1}$ | $10^{-2}$ | $10^{-3}$ | $10^{-1}$ | $10^{-2}$ | $10^{-3}$ |
| 4 hours | N.D. | N.D. | N.D. | 2 | 0 | 0 |
| 6 hours | 0 | 0 | 0 | 3 | 1 | 0 |
| 10 hours | 0 | 0 | 0 | 22 | 7 | 0 |
| 20 hours | 0 | 0 | 0 | 91 | 10 | 0 |
| 24 hours | 0 | 0 | 0 | 107 | 18 | 2 |
| 28 hours | 0 | 0 | 0 | 190 | 58 | 7 |

| | CELL | | | | | |
|---|---|---|---|---|---|---|
| Time P.I. | TEAC | | | Control | | |
| | Und. | $10^{-1}$ | $10^{-2}$ | Und. | $10^{-1}$ | $10^{-2}$ |
| 4 hours | N.D. | N.D. | N.D. | 20 | 9 | 4 |
| 6 hours | 12 | 2 | 5 | 16 | 7 | 7 |
| 10 hours | 13 | 3 | 0 | 48 | 12 | 2 |
| 20 hours | 42 | 5 | 0 | W.O. | W.O. | W.O. |
| 24 hours | 58 | 32 | 10 | W.O. | W.O. | W.O. |
| 28 hours | W.O. | TMTC | 15 | W.O. | W.O. | W.O. |

W.O. = wiped out
TMTC = Too many to count

Experiment 1L

Monolayer cultures of Vero cells were infected with the McKrae strain of HSV-1. After the virus adsorption, the cultures were divided into two sets. One set received maintenance media with 20 mg/ml TEAC and the other set received the same media, but without the TEAC. At 30 min., 6 hr. and 24 hr. post infection, both experimental and control cultures were harvested. The cells were gently scraped and centrifuged.

The pellet was cut into 3 pieces that were double fixed in 2.5% glutaraldehyde and 1% osmium tetraoxide. The cells were dehydrated in a series of increasing alcohol content solutions and embedded in Epon 812. One block of each series was used to cut thick sections for light microscopy. Sections one micron thick from each block were stained with toluidine blue and examined under a light microscope to select an area for electron microscope (EM) observation. The selected area contained normal and infected cells in comparative amounts. The percentage of cells exhibiting cytopathic effects is shown in Table 11.

TABLE 11
PERCENTAGE OF CELLS EXHIBITING CPE
AREA OF INFECTION PER FIELD

| Time P.I. | Virus Control | Virus and Drug |
|---|---|---|
| 30 mins. | scattered | N.D. |
| 6 hours | ½ | 1/6 |
| 30 hours | ½ | scattered |

N.D. = not detectable

Both virus control and drug-treated cultures, at 6 hours post infection, had formed dense intranuclear bodies. In the control group, the dense bodies were from 43 to 60A in size. At 6 hours post infection, the intranuclear bodies were more numerous and ranged in size from 43 to 70 A. The drug-treated cells at 6 hours post infection also showed the formation of intranuclear bodies and the cell membrane was unusually extended and wavy. There was no striking difference in the number of cells containing intranuclear dense bodies in the control cells and the drug-treated cells at 6 hours post infection. However, the extended and wavy appearance of the cytoplasma membrane in the drug-treated cultures was of interest.

At 24 hours post infection, the control group showed nucleocapsids in the nuclei of the cells and the virus particles budding from the cell membrane. Numerous complete virions in the extracellular space were also observed.

In contrast, the TEAC-treated cells at 24 hours post infection showed some nucleocapsids of about 99.6/A in size and several virions with coil-like cores in vacuoles. In the intercellular space, some abnormal virus particles were detected and the cytoplasma membrane in these cultures continued to be extended and wavy. Some of these TEAC-treated cells had coreless nucleocapsids in paracrystalline arrays in their cytoplasma. The relative number of cells exhibiting these changes is illustrated in Table 12 below.

TABLE 12
EM EXAMINATION OF TREATED
AND NON-TREATED CELLS

| Time P.I. | No. of Cells Examined | Internuclear Dense Bodies | Virus Particles | Total % |
|---|---|---|---|---|
| | | CONTROL | | |
| 30 min. | 100 | 6 | 0 | 6% |
| 6 hours | 100 | 14 | 0 | 14% |
| 24 hours | 50 | 0 | 50 | 100% |
| | | TEAC TREATED | | |
| 30 min. | N.D. | N.D. | N.D. | — |
| 6 hours | 100 | 12 | 0 | 12% |
| 24 hours | 300 | 12 | 8 | 6% |

These observations indicate that the antiviral activity of TEAC may be due to an impairment or block in the assembly of the viral components but not in their production.

C. THIRD SERIES

In the experiments of the third series, it was investigated whether the antiviral activity of TEAC was shared by all quaternary ammonium compounds. Confluent monolayer cultures of Vero cells were infected with the appropriate amount of HSV-2. The 333 strain of HSV-2, which can be obtained from ATCC, was used and allowed to adsorb for 30 minutes prior to the addition of the drug.

Experiment 1M

In this experiment, 25 mg/ml HMB was tested on Vero cells infected with HSV-2. The virus control cultures, without HMB, had 705 plaque. The HMB-treated cultures had 142 plaque and a thin cell layer. Consequently, 80% plaque inhibition was achieved in the cell cultures treated with HMB.

Experiment 1N

In this experiment, 20 mg/ml of HMB was tested on Vero cells infected with HSV-2, 20 mg/ml of HMB gave complete inhibition of plaque. The number of plaque on the virus control was about 10 to 12 plaque.

Experiment 1O

In this experiment, 25 mg/ml, 20 mg/ml, and 15 mg/ml of HMB concentrations were tested on Vero cells infected with HSV-2. The results were: 15 mg/ml did not have any effect. The experimental flasks had as many, or more, plaque as the control, with an average of 154 plaque for the control and 169 plaque for the HMB-treated flasks.

At 20 mg/ml HMB, there were no plaque.

At 25 mg/ml HMB, the HMB was toxic to the monolayer. Hence, although there were no plaque, the lack of plaque was most likely due to toxicity rather than antiviral activity. In this experiment, the bottles were stained at a later time than in other experiments because the control grew slowly.

Experiment 1P

HMB was further tested at a concentration of 20 mg/ml of reinfected Vero cells. The control flasks had an average of 89 plaque and the HMB-treated flasks had an average of 7 to 8 plaque. This represented a plaque inhibition of 91%.

EXAMPLE NO. 2

In this experiment, TEAC was tested against a non-herpetovirus to determine whether its antiviral activity (and, therefore, that of quaternary ammonium compounds as a group) was HSV specific or whether the antiviral activity extended to viruses as a whole. For this purpose, the virus vacinnia was chosen.

Confluent monolayer cell cultures of Vero cells were infected with the 333 strain of vaccinia. After adsorption of the virus, maintenance media containing TEAC was added to the flasks. The same maintenance media without the TEAC was added to the control flasks. The flasks were treated with TEAC concentrations of 25 mg/ml, 20 mg/ml, 15 mg/ml, and 10 mg/ml. After 36–48 hours incubation, the plates were stained and the plaque were counted.

The flasks containing 25 mg/ml, 20 mg/ml, and 15 mg/ml of TEAC did not have any plaque, but the layers were also noted to be thin. The flasks containing 10 mg/ml of TEAC exhibited only 2 or 3 plaque per flask visible under the microscope. Hence, at 10 mg/ml of TEAC, 100% inhibition of viral growth of the vaccinia occurred. The control flasks, in contrast, exhibited well defined plaque averaging 150-160 plaque.

EXAMPLE NO. 3

In Vivo Experiments

Female guinea pigs (obtained from Charles River, Inc.) weighing approximately 200 g were used as a model for HSV-2 skin lesions. The animals were anesthetized with 0.15 ml of Ketamine-Rompum mixture. The animals were first shaved on their back with a hair clipper and then treated with a depilatory cream (Nair). The denuded area was washed well and then dried. A tuberculin tyne was washed with ethanol and air dried.

Two methods were tried for infecting the animals with the virus. In one, a drop of HSV-2 suspension was placed on the skin and the skin was punctured with the tyne. In the second method, the tyne was dipped in the virus suspension before puncturing the skin. The first method gave better results and, therefore, was adopted.

Lesions were evident 4 days after infection.

The vesicles had an erythematous base and they were elevated with a blistering appearance. When the vesicles ruptured, a crust formed. The lesions resolved by day 9 or 10 post infection.

In the first experiment, each of 3 guinea pigs was infected on three areas of their backs. At 3 days post infection, treatment was begun on one side of each animal, leaving the other side untreated as a control.

The TEAC treatment was 4 times daily. The animals were examined daily for vesicles (V), crust (C) and for erythema (R) alone. Lesions on the drug-treated areas did not crust but appeared to be faded by 6 days post infection (pi) or day 3 after treatment. At day 4 after treatment, a rash appeared. Since it was not present in any other area, this dermatitis was probably due to the TEAC or its vehicle or both.

In the next experiment, 6 guinea pigs were infected in the same manner as the initial 3 guinea pigs. Treatment was begun 12-16 hours post infection. Three animals were treated with TEAC ointment, while the other three served as controls. Lesions showing an erythematous base with either a blister or a crust on top were considered to be HSV specific. These criteria were used because dermatitis made readings difficult. Both the control animals and treated animals were carefully read in the same manner. There was a marked difference between the two groups, not only in the number of lesions but also in their appearance. The results relating to the number of lesions are provided in Table 13.

TABLE 13

| | REDUCTION OF LESIONS BY TEAC # of lesions | | |
|---|---|---|---|
| Days P.I. | Control | TEAC Treated | Percent Reduction |
| 3 | 19 | 15 | 21.0 |
| 4 | 40 | 29 | 27.5 |
| 5 | 41 | 17 | 58.5 |
| 6 | 36 | 15 | 58.3 |

Thus, regardless of whether the animals were treated 3 pi or treated 12-16 hours pi, the TEAC was very effective in treating or preventing the HSV-2. When given 3 days pi, the vesicles did not crust; rather, they reduced in elevation and eventually resolved. When the TEAC was given early, 12-16 hours post infection, less vesicles formed. Not only was there a significant reduction in the number of lesions, but also in their size. Moreover, the lesions neither ruptured nor crusted. As is evident from the experiments, the TEAC had a significant effect in reducing the number and size of HSV-2 lesions, as well as inhibiting the rupture and crusting up the HSV-2 lesions.

EXAMPLE NO. 4

Clinical Tests

Clinical Case A

Patient A is a 43 year old female who first report with a history of herpetic lesions on her buttocks which had erupted approximately every 30 days for several years previously (over a 10 year period, with increasing frequency during the past 2 years). She was referred by a board certified dermatologist who had diagnosed HSV type 2 and who had treated the lesions of at least five attacks with steroid injections. The lesions usually lasted from between seven days to six weeks. The patient experienced periodic pain in the buttocks with chronic severe sciatic pain radiating down her right leg.

Patient A appeared for treatment two days following the latest eruption of lesions on her buttocks. She weighed 57 kg. and was administered 2.8 cc. of a solution of 100 mg of TEAC per cc. of normal saline. (This solution was used in all parenteral administrations described herein.) At the time of treatment she experienced some blurred vision and slight dizziness on rising to the seated position. However, immediately following the infusion she reported cessation of sciatic pain.

The patient called approximately three weeks later reporting that she was asymptomatic. She subsequently reported that she had gone 52-53 days without lesions or pain at which time a few vesicles had appeared without weeping or crusting and disappeared in two to three days without pain.

Two months after the initial exam, the patient reported that several small lesions had developed on the previous day with mild sciatic pain. She was given a second infusion of 3.2 cc. Immediately after this treatment she experienced some blurred vision but the sciatic nerve pain disappeared during the infusion.

Three days later, the patient had 6 to 8 patches of lesions developing over a larger area with some pain but no vesicles had developed yet. The patient also had pain in the back and down both legs.

Two days later, the patient was given a third infusion of 3.4 cc.

Approximately two weeks later, the patient reported a few tiny areas under the skin but without eruptions and the tiny areas disappeared in about a day. About three weeks later there was no further pain or lesions. About three weeks later, the patient continued to be trouble free. About one week later the patient reported that a few spots came up without aura, and that these were gone in 24 hours.

The patient was last contacted eighteen months after the initial exam at which time she advised that she had experienced no further lesions or pain.

Clinical Case B

Patient B is a 43 year old male diagnosed as having both HSV type 1 (expressed as oral lesions) and HSV type 2 (expressed as penile lesions). He weighed 75 kg when he reported and was administered 3.7 cc of TEAC (5 mg/kg). Immediately following infusion, the patient reported blurred vision, dryness of the mouth, and unsteady gait; however, these drug related effects ceased 10-15 min. after cessation of infusion.

In a call to the patient 3 days later he reported that his oral lesions had been resolved, resolution occurring in a shorter than usual time.

About three weeks later, the patient described a labial aura and predicted a massive outbreak. He was administered an additional 3.7 cc. The following day the patient reported an absence of an aura and no occurrence of the expected lesion except for a very small lesion at the corner of the mouth which was cultured out as HSV-1. About a month later the patient reported a "chapped lip-like" area but that the attack was never serious and that no lesion appeared.

Five weeks after the previous treatment, the patient returned for treatment of acute penile lesions of HSV type 1 and 2. He was administered 4.5 cc (6.0 kg/mg). Eight days later, the patient reported that the lesion had dried the next day and crusted and disappeared in 2-3 days. The patient reported feeling that his active lesions obviously respond to treatment but that recurrences were not eliminated.

About three days later, lip lesions appeared, and the patient requested further treatment. He was administered 4.8 cc of TEAC. About 5 days later, the patient reported that labial and penile lesions were starting. The patient was contacted about two weeks later, and reported that the last treatment appeared of no value. He reported that he had had painful penile lesions that lasted 8 days. About a month later, however, the patient reported that he had no more attacks, which he attributed in part to the treatment.

Clinical Case C

Patient C is a 26 year old male who weighed 77 kg when he reported for treatment. He was diagnosed as having multiple herpes simplex virus infection since the age of 6 months. He appeared for treatment with labial lesions and a large lesion in the middle of his back. He also had lesions on his forehead. In the past he had lesions nasally. He had at times experienced remissions of 4-5 months.

The patient was infused with 3.85 cc (5 mg/kg) TEAC solution, and experienced slightly blurred vision.

The next day, the patient reported that the lesions were markedly improved, especially on his forehead. Three days later, the patient experienced lesions. However, three additional days later it was acknowledged that two attacks of labial lesions cleared rapidly. A week later, the patient reported having only a few fever blisters that cleared right away. The patient reported the same a week later. No problems were reported until about a month later when the patient reported a lesion on the forehead that crusted relatively quickly. The patient was contacted five months and ten months after the initial treatment reported that he had experienced no further problems.

Clinical Case D

Patient D is a 37 year old female who weighed 56 kg when she reported for treatment. For the past 5 years, she had experienced lesions on her buttocks, with symptoms worsening prior to her menstrual cycle. There was no time she reported when there was a cessation of lesions or auras.

She was administered 2.8 cc TEAC solution 5 mg/kg) and experienced dry mouth and transient blurred vision. Two days later she reported that all lesions were improving and that itching and tingling disappeared with the treatment. The patient was not available for further follow up.

Clinical Case E

Patient E is a 34 year old male who weighed 93 kg when he reported for treatment. He had a history of HSV type 2 penile lesions occurring at least once per month with the lesions sometimes lasting 3 months. He was administered 4.8 cc of TEAC (5 mg/kg), and experienced slightly blurred vision. Two days later, he reported that the lesions had started to crust; however, he then experienced a massive prodome with large weeping lesions which were unlike any lesions of the previous 5 years.

The patient returned two weeks later without lesions but feeling that he was in a "prodome stage." He was administered another 4.8 cc of TEAC solution on that day. The next day he reported no prodome and no lesions, but the following day reported that another breakout was occurring.

A week later, the patient was 99% cleared with 2 pinpoint lesions remaining. He was infused with a further 5 cc of TEAC on that day. Three days later the patient reported only pinpoint sites and felt that each infusion caused a definite change in the disease. Two days later the patient reported that all lesions had cleared up. A few days later, vesicles had appeared which quickly disappeared without crusting, and one new lesion had appeared.

Three days later, the patient reported that the final lesion had gone but that "some lesions are trying to come." Two days later the lesions had not come. A week later, the patient reported that prodome started 3 days earlier with 5-6 pinpoint lesions breaking out on the following day on the right dorsal side of his penis.

Clinical Case F

Patient F is a 31 year old male diagnosed as having HSV type 2 infection of his penis. He reported a history of penile lesions approximately every two months lasting 1-2 weeks. He weighed 75 kg when he reported, and was administered 3.8 cc (5 kg/mg) of TEAC. The next day the patient considered his lesion improved. The following day the patient's dermatologist found a small lesion. Three weeks later the patient noticed a small new lesion.

A month after initial treatment, the patient reported with a lesion on the base of his penis and was administered 4.5 cc of TEAC. Nine days later the patient stated that the lesion had cleared in 48 hours, but on the other side lesions had developed.

The next day the patient was infused with a further 4.0 cc of TEAC. Within 4 days the lesions had cleared up. About 3 weeks later, the patient reported that a new lesion had appeared earlier at the same site, was open for a day or so, and then crusted and that now his general condition was the best it had been for several months and that he was completely cleared up.

Five weeks later, the patient reported that he had had one lesion that lasted a week and another that cleared up quickly and that he was in "good shape." The patient subsequently had lesions that lasted 12 days and 7 days.

Clinical Case G

Patient G is a 36 year old male who weighed 78 kg and was diagnosed as having HSV type 2. He reported that penile lesions had erupted every 2 weeks to 3 months (usually every 1-1½ months) for the previous 7 years. Lesions were acute for 2-3 days followed by 4 days of scarring.

When he reported for treatment, the patient reported experiencing labilais prodrome without lesions and also a sensation in his lower back. He was administered 4.3 cc of TEAC solution on that day. The next day he reported that the treatment to be "great" with the lesions improving, and 2 days later he reported the "lesions" were gone with no crusting, skin smooth, visable capillaries disappeared, softer circumcision scar, no back sensation, psoriasis improved, but some reddening of the lip where the patient had never had a lesion. Three days later he reported everything fine except two pinpoints red spots that the patient did not feel would become vesicles. A week later, the patient reported that the lesions had never crusted and were gone within 48 hours.

After over a month with only a minor tingling incident the patient reported 2 penile lesions and was administered 4.5 cc of TEAC solution. He was also infused with a further 4.5 cc of TEAC the next day. The patient remained relatively stable for about a month; however, after an additional month with no new infusion, the patient was back to his pre-treatment state.

The patient was contacted five months after initial treatment at which time he stated that he was at his pre-treatment state.

Clinical Case H

Patient H is a 41 year old male who weighed 77 kg when he reported. He was diagnosed as having HSV type 2. The patient reported that for the last 2 years he had had penile lesions (lasting 7-10 days) approximately every 2 months. A lesion had started the day before he reported. He was treated with 4.6 cc of TEAC (6.0 mg/kg . The following day the patient reported striking improvement, but experienced a setback 6 days later when the condition became a visual attack. The attack disappeared.

The patient was contacted six months after treatment, at which time he advised that besides 2 minor incidents of red spots (which did not develop) and some aura, he has had no further problems and, in particular, no further vesicles since the attack immediately following his treatment cleared. This patient was contacted again 12 months later at which time he advised that he has had a few minor incidents of red spots that did not develop. He reported his condition as problem free.

Clinical Case I

Patient I is a 42 year old male who weighed 86 kg when he reported for treatment. He was diagnosed as having both HSV types 1 and 2. The patient reported he had had good health until he developed herpetic lesions in and around the mouth, chin and cheeks, unexplained nocturnal headaches, penile lesions and symptoms similar to those of stomach ulcers. He stated his lesions were almost constantly present. He was infused with 4.7 cc of TEAC solution. The next day, the patient reported that a sore had started on his tongue, but had gone by that morning. Four days later the patient reported that the infection tried to come up all over but failed and he was all clear.

About 5 weeks later, the patient reported with a lesion on his chin which had developed the previous day. He also reported a nocturnal headache the previous night. He stated that these were the first problems he had had since his treatment. He was administered a further 4.75 cc TEAC solution (5.5 mg/kg body weight).

Three months later the patient reported that the lesion had cleared 3 days after the infusion and that he had had no further lesions until one developed in the preceding week. He reported that he had had no further nocturnal headaches.

Clinical Case J

Patient J is a 50 year old female who weighed 66 kg when she reported for treatment. She was diagnosed as having HSV type 2. She described a history of sacral lesions during the past 4 years which occurred every 2-3 months. Lesions lasted for 5-30 days. She reported moderate pain, itching and stinging in the sacral region commencing the previous night.

She was infused with 3.6 cc of TEAC (5.5 mg/kg) and experienced some blurred vision immediately following the treatment.

Two days later the patient reported that the pain had disappeared and that the lesions were drying. Five years later the patient reported that blisters had appeared two days previously but had now cleared. Two months after treatment the patient reported tingling blisters a month later she was given TEAC in a 1% concentration in a hydrophilic ointment base for topical administration. The following day she reported that the tingling and redness had gone but that 2 more vesicles had appeared. Three days later the patient reported that all the lesions had dried up.

The patient was again contacted six weeks later when she reported that she had since had one attack but that the lesion had only lasted 3 days. On that occasion the patient had once again applied the ointment. Since then she has had no further attacks.

The patient was contacted 12 months later at which time she advised that she has had a very few minor incidents since treatment, but that she has applied ointment and the problem has resolved itself completely.

Clinical Case K

Patient K is a 34 year old female who weighed 59 kg. when she reported for treatment. She was diagnosed as having HSV type 2. She described a history of lesions on the buttocks and genital region with attacks occurring monthly in cooler weather and weekly in warmer weather. She said her last attack had occurred one week prior to her reporting for treatment. The patient was infused with 3.1 cc, after which she experienced some blurred vision. Three weeks later the patient reported that she felt a massive attack coming. On the same day the patient was administered a further 3.4 cc. of TEAC after which she once again experienced blurred vision. Six weeks later the patient reported that the attack had not occurred. She said that she had since had 2 shorter attacks (of about 2-3 days each) both of which were of a milder severity.

Clinical Case L

Patient L is a 49 year old female who weighed 53 kg. when she reported for treatment. She was referred by a Board Certified Dermatologist who had performed facial dermabrasion on her. She had developed HSV Type 1 lesions throughout the area of the surgery. After the development of the surgical complication, the patient could recall one previous lesion in a localized area some years previously.

The patient was infused with 2.9 cc. of TEAC (5.5 mg/kg) after which she experienced some blurred vision. Four days after treatment the patient reported that she had felt badly for 24–36 hours following the treatment but had since felt quite well.

Three weeks later the patient's referring dermatologist advised that on the 7th day after the treatment, the crusting had all disappeared. He observed that in his experience this would normally have taken 3 weeks until DMSO treatment was introduced, after which time he had still not seen it take less than 2 weeks.

Clinical Case M

Patient M is a 22 year old female with a history of HSV type 1 infections extending over a period of more than 2 years. When she reported for treatment, she described a history of labialis lesions occurring every 2-3 months and lasting approximately 14 days. The lesions would tyically begin as blisters then spread out to a more extensive area. When the patient reported, a lesion had begun 2½ days previously. She was given an ointment containing a 1% concentration of TEAC in a hydrophillic ointment base for topical administration. Five days later, the patient reported that the lesions had cleared in a shorter time period than usual.

Two months later, the patient once again reported that a labialis lesion had developed and that she had once again resumed administration of the ointment. Three days later, the patient reported that the lesion had not spread and had now crusted.

Clinical Conclusions

From the above clinical cases, it is clearly seen that administration of quaternary ammonium compounds was effective in the treatment of HSV types 1 and 2 diseases. The degree of relief and the duration of the relief varied from patient to patient, ranging from a minor short-term effect to complete remission of the disease. In some cases, no significant improvement was reported. Thus, while treatment with a quaternary ammonium compound is not the answer to all HSV problems, it can provide very significant and welcome relief for those patients that do respond.

Conclusions

In the in vitro and clinical experiments, two quaternary ammonium compounds, TEAC and HMB, and three viruses, HSV-1, HSV-2, and vaccinia were selected and tested as representative of quaternary ammonium compounds and viruses. The experiments clearly establish that quarternary ammonium compounds are effective in treating and preventing diseases and infections caused by viruses.

It is intended that the specification and examples be considered as exemplary only with the true scope and spirit of the invention being indicated by the claims.

Because many varying and different embodiments may be made within the scope of the inventive concept herein taught, and because many modifications may be made in the embodiments herein detailed in accordance with the descriptive requirements of the law, it is to be understood that the details herein are to be interpreted as illustrative and not in a limiting sense.

What is claimed is:

1. A method for treating infection or disease in a mammal caused by herpes simplex virus type-1 or herpes simplex virus type-2 comprising the step of administering to the mammal a quaternary ammonium compound selected from the group consisting of tetraethylammonium ion, hexamethonium ion, pentolinium ion, chlorisondamine ion, trimethidinium ion, trimethaphan ion, and homologs thereof in an effective dosage.

2. The method of claim 1, wherein the quaternary ammonium compound is selected from the group consisting of tetraethylammonium ion, hexamethonium ion, and homologs thereof.

3. The method of claim 1, wherein the treatment prevents or reduces the shedding of the herpes simplex virus type-1 or herpes simplex virus type-2 by a mammal infected by the virus.

4. The method of claim 1, wherein the treatment prevents the recurrence of symptoms of a disease in a mammal caused by herpes simplex virus type-2 or herpes simplex virus type-1.

5. The method of claim 1, wherein the treatment reduces the frequency of the recurrence of symptoms of a disease in a mammal caused by herpes simplex virus type-2 or herpes simplex virus type-1.

6. The method of claim 1, wherein the treatment reduces the severity of symptoms of a disease in a mammal caused by herpes simplex virus type-2 or herpes simplex virus type-1.

7. The method of claim 1 wherein the quaternary ammonium compound is a ganglionic blocking agent.

8. A method for treating a mammal comprising the step of administering to the mammal a quaternary ammonium compound selected from the group consisting of tetraethylammonium ion, hexamethonium ion, pentolinium ion, chlorisondamine ion, trimethidinium ion, trimethaphan ion, and homologs thereof in a dosage effective to produce an anti-viral effect with respect to herpes simplex virus type-2 or herpes simplex virus type-1.

9. The method of claim 8, wherein the quaternary ammonium compound is selected from the group consisting of tetraethylammonium ion, hexamethonium ion, and homologs thereof.

10. The method of claim 8, wherein quaternary ammonium compound is a ganglionic blocking agent.

11. A method of treating a mammal comprising the step of administering to the mammal a quaternary ammonium compound selected from the group consisting of tetraethylammonium ion, hexamethonium ion, pentalonium ion, chlorisondamine ion, trimethidinium ion, trimethaphan ion, and homologs thereof in a dosage effective to inhibit the viral function of herpes simplex virus type-2 or herpes simplex virus type-1.

12. The method of claim 11, wherein the quaternary ammonium compound is selected from the group consisting of tetraethylammonium ion, hexamethonium ion, and homologs thereof.

13. The method of claim 11, wherein the quaternary ammonium compound is a ganglionic blocking agent.

* * * * *